United States Patent [19]
Chien et al.

[11] Patent Number: 5,891,114
[45] Date of Patent: Apr. 6, 1999

[54] SOFT-TIP HIGH PERFORMANCE BRAIDED CATHETER

[75] Inventors: Thomas Yung-Hui Chien, San Jose; Lex P. Jansen, Pleasanton; Henry Nita, Milpitas; Jeffrey A. Sarge, Fremont, all of Calif.

[73] Assignee: Target Therapeutics, Inc., Fremont, Calif.

[21] Appl. No.: 941,511

[22] Filed: Sep. 30, 1997

[51] Int. Cl.$^6$ .................................................... A61M 25/00
[52] U.S. Cl. ........................................ 604/282; 138/123
[58] Field of Search ................................. 604/282, 281, 604/280, 264; 138/123

[56] References Cited

U.S. PATENT DOCUMENTS

| | | |
|---|---|---|
| 243,396 | 6/1881 | Pfarre . |
| 2,211,975 | 8/1940 | Hendrickson . |
| 2,407,929 | 9/1946 | Jeckel . |
| 2,437,542 | 3/1948 | Krippendorf . |
| 2,472,483 | 6/1949 | Krippendorf . |
| 3,174,851 | 3/1965 | Buehler et al. . |
| 3,351,463 | 11/1967 | Rozner et al. . |
| 3,416,531 | 12/1968 | Edwards . |
| 3,753,700 | 8/1973 | Harrison et al. . |
| 3,757,768 | 9/1973 | Kline . |
| 3,924,632 | 12/1975 | Cook . |
| 4,425,919 | 1/1984 | Alston, Jr. et al. . |
| 4,430,083 | 2/1984 | Ganz et al. . |
| 4,484,586 | 11/1984 | McMickle et al. . |
| 4,516,972 | 5/1985 | Samson . |
| 4,577,543 | 3/1986 | Wilson . |
| 4,657,024 | 4/1987 | Coneys . |
| 4,676,229 | 6/1987 | Krasnicki et al. . |
| 4,737,153 | 4/1988 | Shimamura et al. . |
| 4,739,768 | 4/1988 | Engelson . |
| 4,806,182 | 2/1989 | Rydell et al. . |
| 4,817,613 | 4/1989 | Jaraczewski et al. . |
| 4,830,059 | 5/1989 | Silberstang . |

(List continued on next page.)

FOREIGN PATENT DOCUMENTS

| | | |
|---|---|---|
| 0098100 | 1/1984 | European Pat. Off. . |
| 0421650 A1 | 4/1991 | European Pat. Off. . |
| 2613231 | 10/1988 | France . |
| 3242449 | 5/1983 | Germany . |
| 3642107 | 6/1987 | Germany . |
| 2-283346 | 11/1990 | Japan . |
| 3-023830 | 1/1991 | Japan . |
| 5-56910 | 5/1993 | Japan . |
| 5-220225 | 8/1993 | Japan . |
| WO 93/05842 | 4/1993 | WIPO . |
| WO 93/15785 | 8/1993 | WIPO . |

*Primary Examiner*—John D. Yasko
*Attorney, Agent, or Firm*—Morrison & Foerster LLP

[57] ABSTRACT

This is a catheter assembly which may be used in accessing a tissue target within the body, typically a target which is accessible through the vascular system. Central to the invention is the use of a braided metallic reinforcing member, typically of a stainless steel or super-elastic alloy ribbon, situated within the catheter body in such a way to create a catheter section having a thin wall, controlled stiffness, and high resistance to kinking. The distal-most section of the catheter is much more flexible than are other braided catheters of the genre due to choice of braid construction features of that distal-most section. The distal-most braid, and optionally, intermediate braid components are constructed to be more flexible than the more proximal sections due to deletion of ribbons from the braid structure, change of ribbon material, and change of pitch. The various sections include braids which may have a consistent pitch or may vary in pitch along the axis of the catheter or catheter section. The braided ribbon reinforcing member typically is placed between a flexible outer tubing member and an inner tubing member to produce a catheter section which is very flexible but highly kink resistant. The more proximal sections of the catheter assembly are often substantially stiffer than the more distal sections also due to the presence of stiff polymeric tubing or composited materials in the stiffer section.

31 Claims, 5 Drawing Sheets

U.S. PATENT DOCUMENTS

| | | |
|---|---|---|
| 4,832,681 | 5/1989 | Lenck . |
| 4,899,787 | 2/1990 | Ouchi et al. . |
| 4,981,478 | 1/1991 | Evard et al. . |
| 4,985,022 | 1/1991 | Fearnot et al. . |
| 5,037,404 | 8/1991 | Gold et al. . |
| 5,057,092 | 10/1991 | Webster, Jr. . |
| 5,069,674 | 12/1991 | Fearnot et al. . |
| 5,176,660 | 1/1993 | Truckai . |
| 5,176,661 | 1/1993 | Evard et al. . |
| 5,178,158 | 1/1993 | de Toledo . |
| 5,180,376 | 1/1993 | Fischell . |
| 5,184,627 | 2/1993 | de Toledo . |
| 5,217,482 | 6/1993 | Keith . |
| 5,222,949 | 6/1993 | Kaldany . |
| 5,248,305 | 9/1993 | Zdrahala . |
| 5,251,640 | 10/1993 | Osborne . |
| 5,279,596 | 1/1994 | Castaneda et al. . |
| 5,313,967 | 5/1994 | Lieber et al. . |
| 5,334,169 | 8/1994 | Brown et al. . |
| 5,336,205 | 8/1994 | Zenzen et al. . |
| 5,405,338 | 4/1995 | Kranys . |
| 5,451,209 | 9/1995 | Ainsworth et al. . |
| 5,465,710 | 11/1995 | Miyagi et al. . |
| 5,533,987 | 7/1996 | Pray et al. . |
| 5,538,513 | 7/1996 | Okajima . |
| 5,569,220 | 10/1996 | Webster ................................ 604/282 |
| 5,702,373 | 12/1997 | Samson ................................ 604/282 |
| 5,755,704 | 5/1998 | Lunn ..................................... 604/282 |
| 5,782,811 | 7/1998 | Samson et al. ....................... 604/282 |

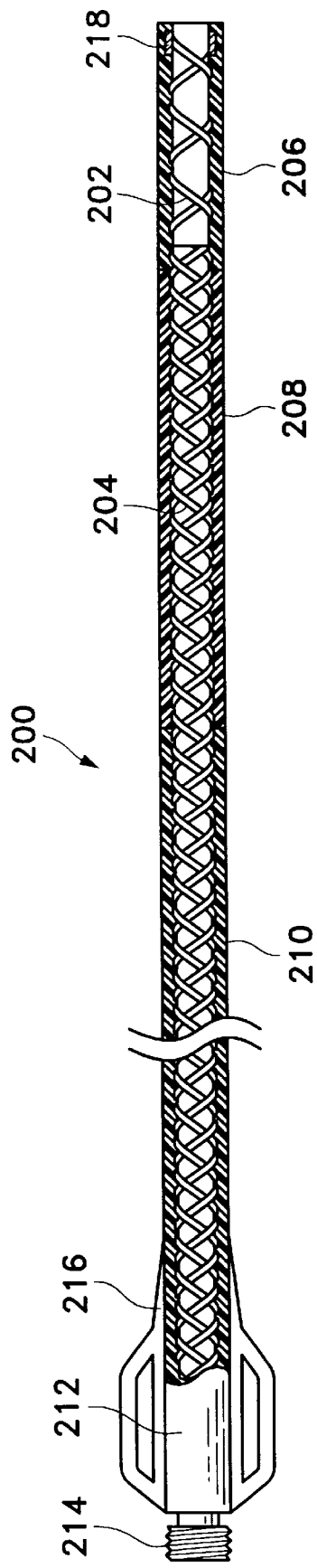
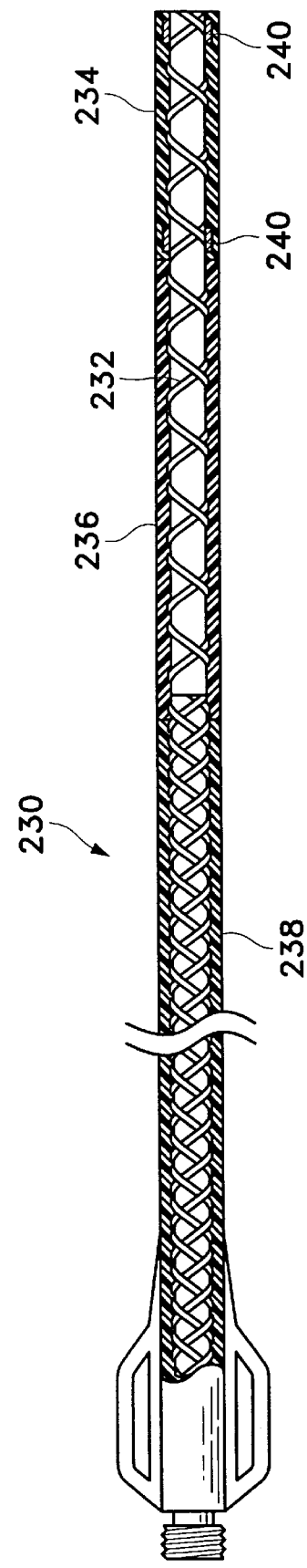

SOFT-TIP HIGH PERFORMANCE BRAIDED CATHETER

FIELD OF THE INVENTION

This invention is a surgical device. In particular, it is a catheter assembly which may be used in accessing a tissue target within the body, typically a target which is accessible through the vascular system. Central to the invention is the use of a braided metallic reinforcing member, typically of a stainless steel or super-elastic alloy ribbon, situated within the catheter body in such a way to create a catheter section having a thin wall, controlled stiffness, and high resistance to kinking. The distal-most section of the catheter is much more flexible than are other braided catheters of the genre due to choice of braid construction features of that distal-most section. The distal-most braid, and optionally, intermediate braid components are constructed to be more flexible than the more proximal sections due to deletion of ribbons from the braid structure, change of ribbon material, and change of pitch. The various sections include braids which may have a consistent pitch or may vary in pitch along the axis of the catheter or catheter section. The braided ribbon reinforcing member typically is placed between a flexible outer tubing member and an inner tubing member to produce a catheter section which is very flexible but highly kink resistant. The more proximal sections of the catheter assembly are often substantially stiffer than the more distal sections also due to the presence of stiff polymeric tubing or composited materials in the stiffer section.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially practical. Catheters are also used to access other regions of the body, e.g., genito-urinary regions, for a variety of therapeutic and diagnostic reasons. One such treatment of diseases of the circulatory system is via angioplasty (PCA). Such a procedure uses catheters having balloons on their distal tips. It is similarly common that those catheters are used to deliver a radio-opaque agent to the site in question prior to the PCA procedure to view the problem prior to treatment.

Often the target which one desires to access by catheter is within a soft tissue such as the liver or the brain. These are difficult sites to reach. The catheter must be introduced through a large artery such as those found in the groin or in the neck and then be passed through ever-narrower regions of the arterial system until the catheter reaches the selected site. Often such pathways will wind back upon themselves in a multi-looped path. These catheters are difficult to design and to utilize in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above and yet at the same time not cause significant trauma to the blood vessel or to the surrounding tissue. Further details on the problems and an early, but yet effective, way of designing a catheter for such a traversal may be found in U.S. Pat. No. 4,739,768, to Engelson. These catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established.

There are other ways of causing a catheter to proceed through the human vasculature to a selected site, but a guidewire-aided catheter is considered to be both quite quick and somewhat more accurate than the other procedures. One such alternative procedure is the use of a flow-directed catheter. These devices often have a small balloon situated on the distal end of the catheter which may be alternately deflated and inflated as the need to select a route for the catheter is encountered.

This invention is an adaptable one and may be used in a variety of catheter formats. The invention utilizes the concept of combining one or more polymeric tubes with a metallic braid comprising ribbons of a super-elastic alloy. The construction technique has the benefit of producing catheter sections having small overall diameters but with exceptional strength, resistance to kinking, and recovery from kinking (even in vivo) should such kinking occur. This catheter may be used in conjunction with a guidewire, but the catheter body may also be used as a flow-directed catheter with the attachment of a balloon or in combination with a specifically flexible tip, as is seen, for instance, in U.S. Pat. No. 5,336,205 to Zenzen et al., the entirety of which is incorporated by reference.

The use of braids in a catheter body is not a novel concept. Typical background patents are discussed below. However, none of these documents have used our concept to produce a catheter which has the physical capabilities of the catheter of this invention.

MULTI-WRAP CATHETERS

There are a number of catheters discussed in the literature which utilize catheter bodies having multiply-wrapped reinforcing material. These catheters include structures having braided bands or ones in which the spirally wound material is simply wound in one direction and the following layer or layers are wound in the other.

Krippendorf, U.S. Pat. No. 2,437,542, describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet flexible. The thus-plasticized tubing is then dipped in some other medium to allow the formation of a flexible varnish-like layer. This latter material may be a tung oil base or a phenolic resin and a suitable plasticizer. There is no indication that this device is of the flexibility described herein. Additionally, it appears to be the type which is used in some region other than in the body's periphery or in its soft tissues.

Similarly, U.S. Pat. No. 3,416,531, to Edwards, shows a catheter having braiding-edge walls. The device further has additional layers of other polymers such as TEFLON and the like. The strands found in the braiding in the walls appear to be threads having circular cross-sections. There is no suggestion of constructing a device using ribbon materials. Furthermore, the device is shown to be fairly stiff in that it is designed so that it may be bent using a fairly large handle at its proximal end.

U.S. Pat. No. 3,924,632, to Cook, shows a catheter body utilizing fiberglass bands wrapped spirally for the length of the catheter. As is shown in FIG. 2 and the explanation of the Figure at column 3, lines 12 and following, the catheter uses fiberglass bands which are braided, that is to say, bands which are spiraled in one direction cross over and under bands which are spiraled in the opposite direction. Additionally, it should be observed that FIG. 3 depicts a catheter shaft having both an inner lining or core 30 and an outer tube 35.

U.S. Pat. No. 4,425,919, to Alston, Jr. et al., shows a multilayered catheter assembly using multi-stranded flat wire braid. The braid 14 in FIG. 3 further covers an interior tubing or substrate 12.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is preferably made of an annealed copper wire which has been coated with a body-compatible polymer such as a polyurethane or a silicone. After coating, the copper wire is wound into a tube. The wound substrate is then coated with still another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is a polyaramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use with a guidewire. It would not meet the flexibility criteria required of the inventive catheter described herein.

U.S. Pat. No. 4,806,182, to Rydell et al, shows a device using a stainless steel braid imbedded in its wall and having an inner layer of a polyfluorocarbon. The process also described therein is a way to laminate the polyfluorocarbon to a polyurethane inner layer so as to prevent delamination.

U.S. Pat. No. 4,832,681, to Lenck, shows a method and apparatus useful for artificial fertilization. The device itself is a long portion of tubing which, depending upon its specific materials of construction, may be made somewhat stiffer by the addition of a spiral reinforcement comprising stainless steel wire.

U.S. Pat. No. 4,981,478, to Evard et al., discloses a multi-sectioned or composite vascular catheter. The interior section of the catheter appears to have three sections making up the shaft. The most interior (and distal) section, 47, appears to be a pair of coils 13 and 24 having a polymeric tubing member 21 placed within it. The next, more proximal, section is 41, and FIG. 4 shows it to be "wrapped or braided" about the next inner layer discussed just above. The drawing does not show it to be braided but, instead, a series of spirally wrapped individual strands. Finally, the outermost tubular section of this catheter core is another fiber layer 49, of similar construction to the middle section 26 discussed just above.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the use of ribbon, nor is any specific mention made of the particular uses to which the Gold et al. device may be placed.

U.S. Pat. No. 5,057,092, to Webster, Jr., shows a catheter device used to monitor cardiovascular electrical activity or to electrically stimulate the heart. The catheter uses braided helical members having a high modulus of elasticity, e.g., stainless steel. The braid is a fairly complicated, multi-component pattern shown very well in FIG. 2.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and is wound at a tension of about 250,000 lb./in.$^2$ or more. The flat strands themselves are said to have a width of between 0.006 and 0.020 inches and a thickness of 0.0015 and 0.004 inches. There is no suggestion to use these concepts in devices having the flexibility and other configurations described below.

Another variation which utilizes a catheter wall having helically placed liquid crystal fibrils is found in U.S. Pat. No. 5,248,305, to Zdrahala. The catheter body is extruded through an annular die, having relatively rotating inner and outer mandrel dies. In this way, the tube containing the liquid crystal polymer plastic-containing material exhibits a bit of circumferential orientation due to the rotating die parts. At column 2, line 40 and following, the patent suggests that the rotation rate of the inner and outer walls of the die may be varied as the tube is extruded, with the result that various sections of the extruded tube exhibit differing stiffnesses.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

Japanese Kokai 05-220,225, owned by the Terumo Corporation, describes a catheter in which the torsional rigidity of the main body is varied by incorporating onto an inner tubular section 33, a wire layer which is tightly knitted at the proximal section of the catheter and more loosely knitted at a midsection.

SINGLE-LAYER. REINFORCED CATHETERS

There are a variety of catheters which, unlike the devices discussed above, utilize but a single layer of reinforcing material.

For instance, U.S. Pat. No. 243,396 to Pfarre, patented in June of 1881, shows the use of a surgical tube having a wire helix situated within the tube wall. The wire helix is said to be vulcanized into the cover of the device.

U.S. Pat. No. 2,211,975, to Hendrickson, shows a similar device also comprising a stainless steel wire 15 embedded in the inner wall of a rubber catheter.

U.S. Pat. No. 3,757,768, to Kline, shows a "unitary, combined spring guide-catheter that includes an inner wall portion formed as a continuous helical spring with the helices in contact with each other and an outer wall portion formed from an inert plastic material enclosing the spring in such a manner as to become firmly bonded to the spring while having its outer surface smooth". There is no suggestion to separate the windings of the coil in any fashion.

U.S. Pat. No. 4,430,083 describes a catheter used for percutaneous administration of a thrombolytic agent directly to a clot in a coronary artery. The device itself is an elongated, flexible tube supported by helically wound wire having a specific cross-sectional shape. The wire is wound into a series of tight, contiguous coils to allow heat shrinking of tubing onto the outside of the wire of the shape of the outer surface of the wire as wound into the helix provides the heat-shrunk tubing with footing for a tight fit.

U.S. Pat. No. 4,657,024, to Coneys, shows a catheter which employs a set of helical strips within the wall of the catheter. However, the helical strips are of a radio-opaque material, e.g., fluorinated ethylene-propylene. It is not clear that the blended radio-opaque material necessarily provides any physical benefit other than the ability to allow the catheter shaft to be seen when viewed with a fluoroscope.

U.S. Pat. No. 4,737,153, to Shimamura et al., describes a device which is characterized as a "reinforced therapeutic tube" and which uses a spiral reinforcing material embedded within the wall of the device.

U.S. Pat. No. 5,069,674, to Fearnot et al. (and its parent, U.S. Pat. No. 4,985,022), shows a small diameter epidural catheter having a distal tip made up of a stainless steel wire which is helically wound and placed within a tubular sheath or tube. There is no suggestion within the patent that the interior coil be made to adhere to the outer tubular sheath.

Similarly, U.S. Pat. No. 5,178,158, to de Toledo, shows what is characterized as a "convertible wire for use as a guidewire or catheter". The patent describes a structure which comprises an interior wire or spring section shown, in the drawings, to be of generally rectangular cross-section. Outer layers of the device include a polyamide sheath placed adjacent to the helical coil at the proximal end of the catheter (see column 4, lines 64 and following). The device also comprises an outer sheath 40 of Teflon that extends from the proximal end 12 to the distal end 14 of the device. The overlying sheath 40 may extend or overhang at the proximal or the distal end of the catheter. The distal tip portion 13 is said to be "flexible, soft, and floppy". The PCT Published Application corresponding to this patent is WO 92/07507.

U.S. Pat. No. 5,184,627 shows a guidewire suitable for infusion of medicaments to various sites along the guidewire. The guidewire is made up of a helically wound coil having a polyamide sheath enclosing its proximal portion and a Teflon sheath tightly covering the entire wire coil. The coil is closed at its distal end. There is no suggestion that the wire forming the helical core be adhesively attached to its outer coverings.

U.S. Pat. No. 5,313,967, to Lieber et al., shows a medical device, a portion of which is a helical coil which apparently may include an outer plastic sheath in some variations. Apparently, a secondary helix of a somewhat similar design (in that it is formed by rotating a flat wire or the like along its longitudinal axis to form a screw-like configuration) is included within the helical coil to provide axial pushability and torque transmission.

U.S. Pat. No. 5,405,338, to Kranys, describes a helically wound catheter incorporating a shaft component having a helically wound coil with a skin or webbing supported by the coil. The skin or webbing is said to contribute "negligibly to the resistance of the catheter to axially directed compressive forces . . ." The catheter may include an inner, taut skin component.

The PCT application, WO 93/15785, to Sutton et al., describes kink-resistant tubing made up of a thin layer of an encapsulating material and a reinforcing coil. As is shown in the drawings, the supporting material is embedded within the wall of the tubing in each instance.

The PCT application bearing the number WO 93/05842, to Shin et al., shows a ribbon-wrapped catheter. The device is shown as a section of a dilatation catheter. The inner section 34 is a helically wound coil and is preferably a flat wire. See, page 6, lines 25 and following. The coil is then wrapped with a heat-shrunk jacket 34 formed of low-density polyethylene. A lubricious material such as a silicone coating may then be placed on the inner surface of the spring coil to "enhance handling of the guidewire". It is also said, on page 6 of the document, that the "entire spring coil, before it is wound or jacketed, may be coated with other materials such as Teflon to enhance lubricity or provide other advantages. In some embodiments, the spring coil has been plated with gold."

Endoscope Structures

Various endoscopic structures, used primarily in sizes which are larger than endovascular catheters utilize structures including stiffener materials.

U.S. Pat. No. 4,676,229, to Krasnicki et al., describes an endoscopic structure 30 having an ultra-thin walled tubular substrate 31 formed of a lubricious material such as TEFLON. The structure contains a filament supported substrate. The filament is coated with and embedded into a filler material, typically an elastomeric material. A highly lubricious outer coating 35, all as shown in FIG. 2, forms the outer layer of the device. FIG. 3 in Krasnicki et al., describes another variation of the endoscopic device in which a different selection of polymer tubing is utilized but the placement of the filamentary support remains varied in an intermediate material of an elastomer. In some variations of the device, the filament is strongly bonded to the inner tubular substrate using an adhesive 37 "such as an epoxy cement having sufficient bond strength to hold the filament to the substrate as it is deformed into a tight radius." See, column 3, lines 50 and following.

U.S. Pat. No. 4,899,787, to Ouchi et al. (and its foreign relative, German Offenlegungshrifft DE-3242449) describes a flexible tube for use in an endoscope having a flexible, basic tubular core structure made up of three parts. The three parts are an outer meshwork tube, an intermediate thermo-plastic resin tube bonded to the outer meshwork tube, and an inner ribbon made of a stainless steel or the like which is adherent to the two polymeric and meshwork tubes such that the resin tube maintains an adherent compressive pressure in the finished flexible tube. The patent also suggests the production of an endoscope tube having "flexibility which varies in step-wise manner from one end of the tube to the other . . . [and is produced] by integrally bonding two or more thermoplastic resin tube sections formed of respective resin materials having different hardnesses to the outer surface of the tubular core structure . . .". See, column 2, lines 48 and following.

U.S. Pat. No. 5,180,376 describes an introducer sheath utilizing a thin, flat wire metal coil surrounded only on its exterior surface with a plastic tube of coating. The flat wire coil is placed there to lower the "resistance of the sheath to buckling while minimizing the wall thickness of the sheath." A variation using two counter-wound metal ribbons is also described.

European Patent Application 0,098,100 describes a flexible tube for an endoscope which uses a helically wound metallic strip having a braided covering contiguous to the outer surface of the coil and having still further out a polymeric coating 9. Interior to the coil is a pair of slender flexible sheaths which are secured to a "front-end piece 10" by soldering.

Japanese Kokai 2-283,346, describes a flexible endoscope tube. The tubular outer shell is made up of two layers of a high molecular weight laminated material. The tube also has an inner layer of an elastic material and interior to it all is a metallic ribbon providing stiffening.

Japanese Kokai 03-023830, also shows the skin for flexible tube used in an endoscope which is made up of a braid 3 prepared by knitting a fine wire of a metal with a flexible portion 2 which is prepared by spirally winding an elastic belt sheet-like material and a skin 4 with which the whole outer surface of the device is covered. The document appears to emphasize the use of a particular polyester elastomer.

Japanese Kokai 5-56,910, appears to show a multi-layered endoscope tube made up of layers of the spiral wound metallic ribbon covered by a polymeric sheath.

French Pat. No. Document 2,613,231, describes a medical probe used with an endoscope or for some other device used to stimulate the heart. The device appears to be a helix having a spacing between 0 and 0.25 mm (See page 4, line 20) preferably rectangular in cross section (See Page 4, Line 1) and of a multiphase alloy such as M35N, SYNTACOBEN, or ELGELOY (See Page 4).

German Offenlegungshrifft DE-3642107 describes an endoscope tube, formed of a spiral tube, a braid formed of fibers interwoven into a net (which braid is fitted on the outer peripheral surface of the spiral tube), and a sheath covering the outer peripheral surface of the braid.

None of the noted devices have the structure required by the claims recited herein.

Other Anti-kinking Configurations

U.S. Pat. No. 5,222,949, to Kaldany, describes a tube in which a number of circumferential bands are placed at regular intervals along a catheter shaft. The bands may be integrated into the wall of the catheter. A variety of methods for producing the bands in the tubular wall are discussed. These methods include periodically irradiating the wall to produce bands of a higher integral of cross-linking.

European Pat. No. Application No. 0,421,650-A1 describes a method for producing a catheter from a roll of polymer film while incorporating other materials such as tinfoil elements or the like.

None of the documents cited above provides a structure required by the disclosure and claims recited below.

SUMMARY OF THE INVENTION

This invention is a catheter assembly having a number of sections, in which the flexibility of the various sections is controlled primarily by selection of the braid characteristics of those sections. Each section is typically made up of an inner liner and an outer covering and a metallic woven ribbon braid located between the liner and the covering. The inner liner may be of a polymeric composition. The inner liner and the outer covering, should they be adjacent the braid and both polymeric, may be selected from polymers which are melt-compatible or melt-miscible with each other. In this way, adjacent polymeric layers hold fast to the braid located between them. Such a combination of polymers, although desirable, is not critical to the inventive concept.

The metallic braid is, in its most basic form, a braid comprising a number of small metallic ribbons wound and treated in such a way that the resulting braid is dimensionally stable and the braided ribbons do not twist. The more basic forms of braids used in this invention desirably, but not critically, are those which are made up of an even number of equally sized ribbons. In such a desired configuration, half of the ribbons are woven in a clockwise direction (as viewed along the axis of the braid) and the remaining half of the ribbons are woven in a counterclockwise direction. The various ribbons may, of course, be of differing size but the sum of the ribbons used in a particular direction should equal those wound in the other direction.

Where used, the super-elastic alloy of choice is one known generically as nitinol. Nitinol is an alloy of nickel and titanium which is blended and heat treated in a specific way to produce an alloy having exceptional resistance to plastic deformation upon physical strain. In addition to nickel and titanium, useful compositions of the alloy may contain a modest amount, up to about 8%, of an Iron Group metal. Suitable for such alloys are ternary alloys containing at least about 1.5% (wt) of one or more alloying members selected from the group consisting of vanadium, chromium, manganese, iron, and cobalt, and particularly chromium or iron.

Each catheter section may additionally have other various layers of polymeric covering and liners as well as metallic tubing members desirably of braid or helical coils. Especially preferred liners comprise polytetrafluoroethylene (TFE or PTFE) polymer. Hydrophilic coatings both on the interior and exterior are additionally contemplated.

The kink resistance of this inventive catheter is due to the presence and composition of the braid in cooperation with the tightly held polymers. In addition to exceptional kink resistance, the catheter may be made in such a way that the wall is extraordinarily thin, particularly when compared to walls of catheters having equal strength but made solely of polymeric materials. The catheter sections including the super-elastic alloy ribbons are additionally very resilient in that, unlike virtually any other commercial catheter, should those catheters section be kinked, the kink is self-healing. This resiliency means that the catheter need not be withdrawn from a patient's vasculature simply because the catheter has inadvertently kinked. Simple movement of the catheter will cure the kink. Kinking minimization is a matter of concern with many catheters in the marketplace today.

In particular, this invention additionally includes catheters in which the most distal section and, optionally, intermediate sections having braids with altered physical parameters such as lowered ribbon density, braid ribbon composition, and pitch. Preferably, the ribbon braid used throughout the catheter is a single structure in which ribbons, preferably in counter wound pairs, are removed to lower stiffness in the more distal sections. The stifftess of the catheter sections may also be lessened by changing the materials making up the braid to, e.g., stainless steels or polymers, in the pertinent section. Changing the pitch of the braid may be accomplished by continuously varying the pitch or by stepwise varying the pitch. The pitch may be varied during production of the braid or by changing the diameter of the braid after production.

The braid used throughout the catheter may be partially constructed of polymeric fibers or carbon fibers either replacing a portion of the metallic ribbons or polymeric fibrous materials or placed in conjunction with a metallic ribbon in the braid. Other metals, e.g., Noble metals such as members of the Platinum Group of the Periodic Table or gold, may be used in the braid itself in much the same way to impart radio-opacity to the braid.

BRIEF DESCRIPTION OF THE DRAWINGS

FIGS. 2, 3., and 4 show, in partial cross-section, various catheter assemblies made according to the invention.

DESCRIPTION OF THE INVENTION

This invention involves a kink-resistant catheter assembly having several sections of differing flexibility. The catheter assembly includes at least two sections, preferably three or more sections, each containing at least an inner liner and a flexible outer member and a braid located between the inner and outer members. The more proximal section preferably includes a super-elastic alloy ribbon braid. The more distal section or sections of the catheter also include woven braid members having physical parameters which are different from those of the proximal section. The physical parameters of the more distal braid members may be varied by changing the number of ribbons in the braid or by changing the composition of the members in that section or by varying the pitch of the members in that section.

The distal catheter section desirably has a critical bend diameter of no more than about 2 mm., and more preferably no more than 1 mm. Desirably, the distal catheter section self-recovers at least 95% of its original "straightness" after it has been subjected to kinking.

Figure 1:
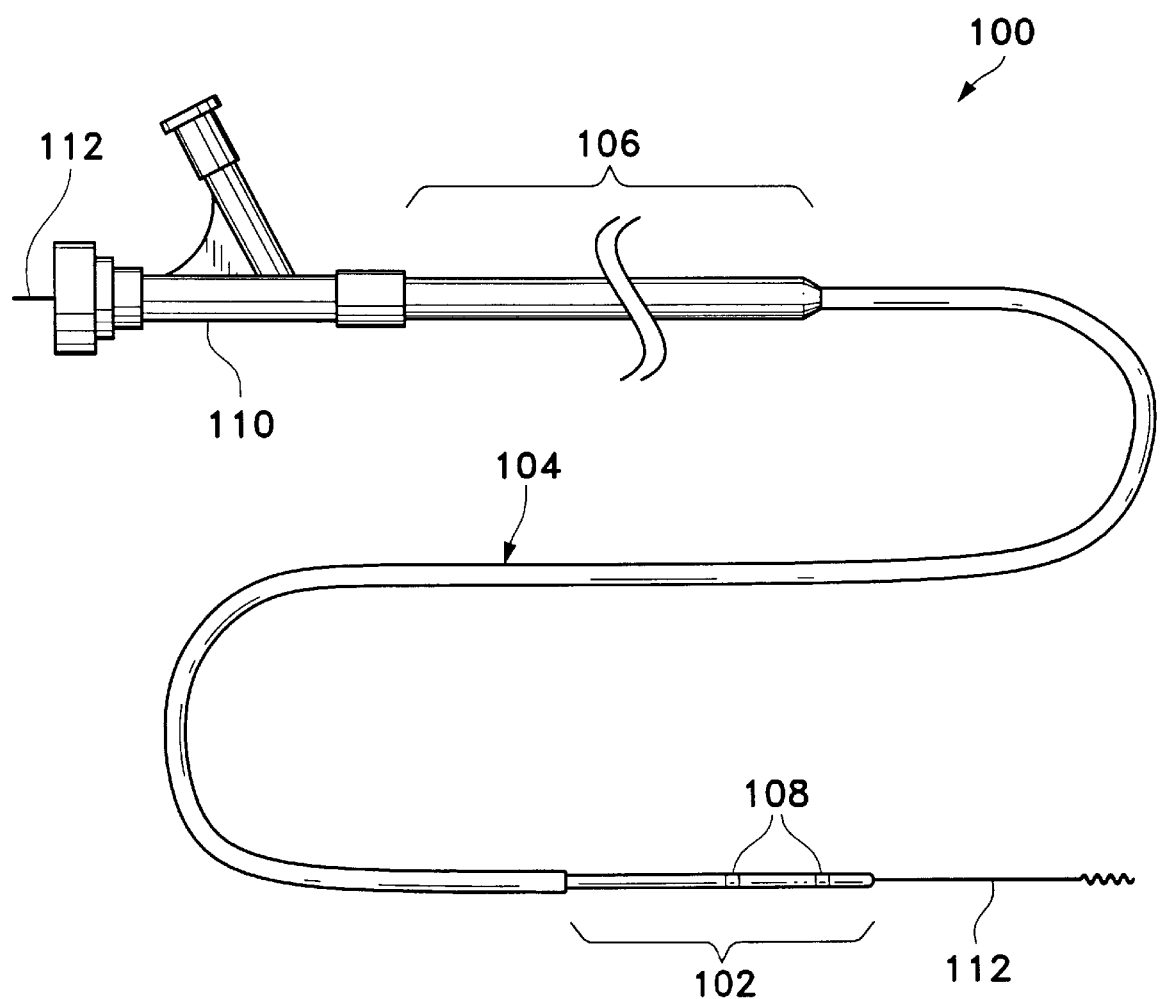
FIG. 1 shows, in side view, a typical three-section catheter made using the concepts of this invention.

One multi-section catheter (100) which may incorporate the concepts of this invention is shown in FIG. 1. Such a catheter is described in more detail in U.S. Pat. No. 4,739,768, to Engelson, (the entirety of which is incorporated by reference) and is particularly suitable for neurological and peripheral vascular applications. Clearly, then, it is also suitable for less demanding service such as might be encountered in access and treatment of the heart. One difficulty which has arisen as higher demands for length have been placed on these catheters is that the diameter of the distal section necessarily becomes smaller and smaller. This is so since the longer catheters must reach ever smaller vascular areas. This smaller diameter requires a concomitant thinning of the wall section. The thinner section walls may kink or ripple when actively pushed along the guidewire or when vaso-occlusive devices are pushed through the catheter's lumen. The typical configuration shown in FIG. 1 has a distal section (102) having significant flexibility, an intermediate section (104) which is typically less flexible, and a long proximal section (106) which in turn is least flexible. The distal section (102) is flexible and soft to allow deep penetration of the extraordinary convolutions of the neurological vasculature without trauma. Various known and often necessary accessories to the catheter assembly, e.g., one or more radio-opaque bands (108) at the distal region to allow viewing of the position of the distal region under fluoroscopy and a luer assembly (110) for guidewire (112) and fluids access, are also shown in FIG. 1. The typical dimensions of this catheter are:

Overall length: 60–200 cm
Proximal Section (106): 60–150 cm
Intermediate Section (104): 20–50 cm
Distal Section (102): 2.5–30 cm Obviously, these dimensions are not particularly critical to this invention and are selected as a function of the malady treated and its site within the body. Typical of the catheters made using this invention are those in the 2 French to 5 French range. The inner diameter of such catheters is then 10 mils to 42 mils.

Furthermore, a catheter made using this inventive concept need not be of three sections increasing stiffness as is shown in FIG. 1. The catheter may be of two discrete sections or may be of four or more discrete sections of differing flexibility. When the catheter is of two sections, the distal and intermediate sections from the above Table are combined to form a catheter having the following dimensions:

Overall length: 82.5–200 cm
Proximal Section: 80–150 cm
Distal Section: 2.5–80 cm Through judicious choice of physical parameters for the catheter sections, the components may also have varying physical parameters (e.g., lubricity, flexibility, wall thickness, inner or outer layer member composition, etc.) within the sections.

Typically, although not necessarily, when a three section catheter is desired, the most proximal section (106) is the "more proximal" or "stiff" section described herein. Again, although not necessarily, when a three section catheter is desired, the most distal section (102) is the "more distal" or "least stiff" section. The mid section (104) may be braided and referred to as "more distal" if the situation warrants it. It is a rare infusion catheter that utilizes a more distal section which is stiffer than any of its more proximal sections.

An additional benefit of the invention is that the use of the super-elastic alloy braid permits the walls of the catheter to be comparatively thinner with no diminution of performance, e.g., crush strength or flexibility, and may provide an improvement in performance.

Figure 4:
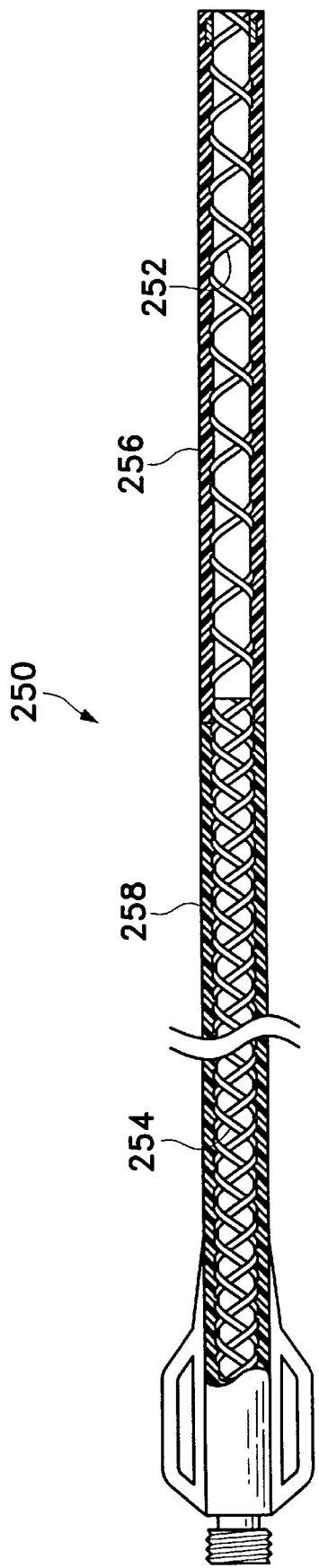

As was noted above, this invention centers on the concept that the distal tip of the catheter contains a braided component and yet that distal tip is exceptionally flexible when compared to the more proximal part of the catheter assembly. FIGS. 2, 3, and 4 each show variations of the invention in which these concepts are applied to catheter assembly.

FIG. 2 shows a catheter assembly (200) which has at least three regions of differing flexibility. The FIG. 2 depiction is a partial cutaway showing a distal braid member 202 and a more proximal braid member (204). As will be explained in more detail below, distal braid member (202) and proximal braid member (204) may share ribbon members in that at least two acceptable ways of producing such a device include weaving a superelastic alloy woven ribbon braid member and mechanically removing a number of those members to form the more flexible section of distal braid member (202). Alternatively, more proximal braid member (204) may be a single structure abutted by an independent but significantly more flexible distal braid (202). Distal braid (202) may, in this instance, be made of a different material than is found in the members making up more proximal braid (204). Additionally, distal braid (202) may have braid member spacing which becomes more spaced distally to promote distal flexibility.

Also shown in FIG. 2 is the use of multiple polymeric coverings having different flexural module. In this instance, most distal section (206) is a quite soft material in keeping with the function of that distal region. The material making up polymeric covering (206) and the other sections of this variation of the invention will be discussed at more length below. In this variation, the distal most end of covering (206) ends at approximately the most distal extension of more proximal braid (204). Obviously, the more proximal braid (204) need not fall exactly on the joint between distal polymeric covering (206) and intermediate polymeric covering (208). It is often wise not to have such junctions coincide because of the difficulty of constructing such joints and because of the possibility that the various joints are coinciding weaknesses in the structure. A slight misalignment of the two junctions is desirable. Intermediate polymeric covering (208) is of a material that typically would have a Shore Hardness which is greater than that of distal polymeric covering (206). Similarly, proximal or the shaft covering (210) is also polymeric and may be of a material which is still significantly harder or of a higher flexible modulus than either of polymeric intermediate covering (208) or distal polymeric covering (206). Also shown in FIG. 2 and the others is a proximal fitting (212) having a threaded coupling (214). Coupling (212) is simply for coupling to other devices and is for passage of guidewires and fluids and the like through the coupling into the catheter assembly and out its distal end. A typical strain reducing member (216) is also shown adjacent coupling member (212). Radio-opaque member (218) is shown most distally placed in catheter assembly (200). Distal marker (218) is placed for the sole purpose of identifying the end of the catheter using fluoroscopy during procedures using this device. It is within the scope of this invention to include more than one radio-opaque band in the region of the distal tip.

The variation shown in FIG. 2 has three regions of distinct and different flexibility. Presumably, because of the construction of the device shown in FIG. 2, the difference between the flexibility of the section encompassed by intermediate polymeric covering (208) would be significantly lower than that dealing with distal section covered by distal polymeric section (206). This would be both due to the difference in flexural modulus between the polymer in covering (208) and that of the polymer found in (206) but, probably more importantly, due to the difference in flexibility between the more distal braid member (204) and the significantly more flexible distal braid member (202).

Each of the variations shown in FIGS. 2, 3, and 4 have central lumens from the proximal end to the distal end. Typically the device will have a single polymeric liner defining that lumen. As noted above, guidewires and other both diagnostic and therapeutic devices and materials flow through this open central lumen out the distal tip of this guidewire assembly. The materials making up the inner liners (not shown) and the outer liners will be discussed in more detail below.

FIG. 3 shows another variation of the inventive catheter assembly (230). In this variation, the more flexible and more distal braid member (232) extends significantly farther proximally than did the variation shown in FIG. 2. The distal polymeric covering (234) and the intermediate polymeric covering (236) might be of approximately the same axial length as those shown in FIG. 2, however. Proximal polymeric covering (238) is typically similar in content and hardness to that component (210) as found in FIG. 2. An independent aspect of this variation of the invention is the presence of dual radio-opaque markers (240) in the distal section of catheter assembly (230). These dual markers may be used in any variation of the invention described herein.

FIG. 4 shows still another variation (250) of the inventive catheter assembly. This variation includes, as did the variation shown in FIG. 3, a comparatively more flexible distal braid component (252) and a comparatively stiffer and more densely woven more proximal braid component (254). This variation of the invention includes only two sections of different external polymer covering. Specifically, the more distal section (256) extends generally for the length of the more distal braid component (252), subject to the above discussion of placement of the various termination portions discussed above. The more proximal polymeric sleeve or covering (258) is similar in length and content to the exterior polymeric coverings (210) in FIG. 2 and (238) in FIG. 3.

This variation (250) of the inventive catheter is desirable in that the more proximal braid section (254) provides both torquability and pushability to the selected site in the human body. The more distal braid (252) provides a modest amount of stiffness but more importantly provides some torquability to the distal section and kink resistance even when being passed through the highly tortuous paths.

Figure 5:
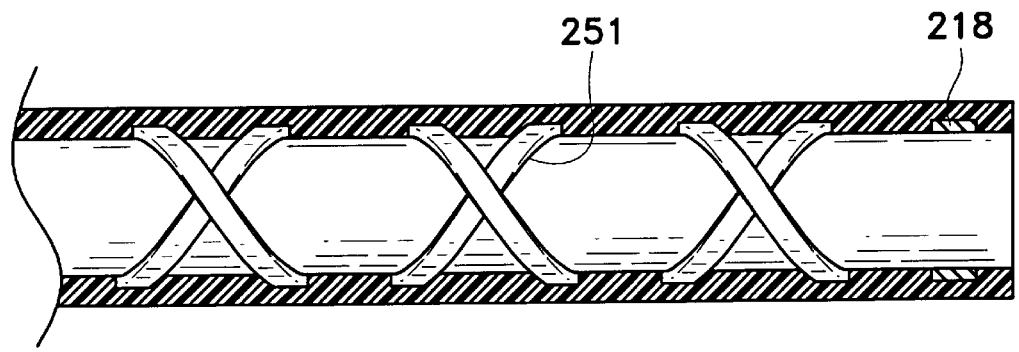
FIGS. 5 and 6 show, in partial cross-section, distal portions of catheter assemblies showing various braid variations.

FIG. 5 shows a close-up cutaway of the distal section of the catheter assembly in which the kink-resisting braid (251) varies in pitch in the section. The pitch becomes wider as the distal end of the section is approached. The flexibility increases toward the distal end.

Figure 6:
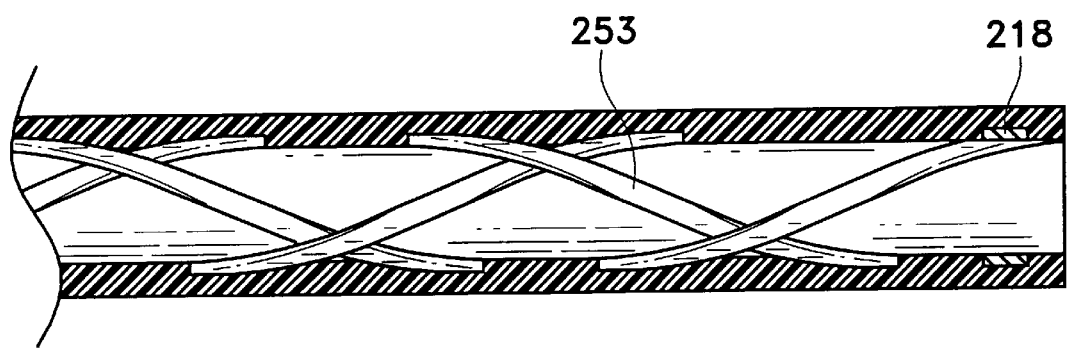

FIG. 6 also shows a close-up cutaway of the distal section of the catheter assembly and illustrates the exceptionally small angle, e.g., 7.5° to the axis or more, which the braid member (253) may take.

Figure 7:
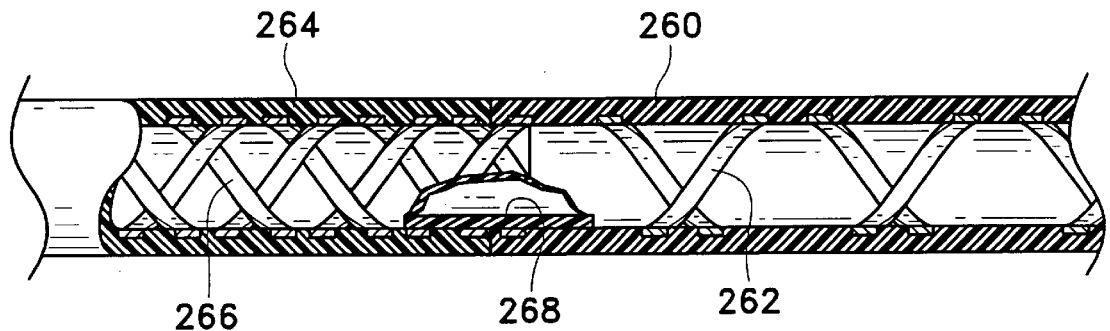
FIGS. 7 and 8 show, in magnification, partial cross-sections of distal portions of catheters assemblies made using this invention.

FIG. 7 provides a close-up partial cutaway of one variation of the distal section of the catheter assembly (200) shown in FIG. 2. In this variation, the more distal polymeric section (260) is shown covering a distal ribbon braid (262). Proximal of distal polymeric covering (260) may be seen polymeric covering (264). More proximal woven ribbon braid (266) is shown to be located proximally of distal ribbon braid (262). As was noted above, more distal ribbon braid (262) may either be an extension of ribbon braid (266) with some of its elements removed or distal ribbon braid (262) may be an independent braid of another material placed distally of woven ribbon braid (266).

The woven metallic braid (266) shown in FIG. 7 is made up of a number of metallic ribbons. A majority of the metallic ribbons in braid (266) are of a member of a class of alloys known as super-elastic alloys.

Preferred super-elastic alloys include the class of titanium/nickel materials known as nitinol—alloys discovered by the U.S. Navy Ordnance Laboratory. These materials are discussed at length in U.S. Pat. Nos. 3,174,851 to Buehler et al., 3,351,463 to Rozner et al., and 3,753,700 to Harrison et al. Commercial alloys containing up to about 8% or more, of one or more other members of the Iron Group of the Periodic Table, e.g., Fe, Cr, Co, are considered to be encompassed within the class of super-elastic Ni/Ti alloys suitable for this service. Desirable alloys containing 1.5–2.5% Cr and having a transition temperature of less than 0° C. are useful.

When using a super-elastic alloy, an additional step may be desirable to preserve the shape of the stiffening braid. For instance, with a Cr-containing Ni/Ti super-elastic alloy which has been rolled into a 1×4 mil ribbon and formed into a 16-member braid, some heat treatment is desirable. Braids which are not treated in this way may unravel during subsequent handling or may undertake changes in diameter or braid member spacing during that handling. In any event, the braid is placed onto a mandrel, usually metallic, of an appropriate size. The braid is then heated to a temperature of 650°–750° F. for a few minutes, possibly (but not necessarily) annealing the constituent ribbon. After heat treatment, the braid retains its shape and the alloy retains its super-elastic properties.

Metallic ribbons that are suitable for use in the more proximal braid (266) of this invention are desirably between 0.25 mil and 3.5 mil in thickness and 2.5 mil and 12.0 mil in width. By the term "ribbon", we intend to include elongated shapes, the cross-section of which are not square or round and may typically be rectangular, oval or semi-oval. They should have an aspect ratio of at least 0.5 (thickness/width). In any event, for super-elastic alloys, particularly nitinol, the thickness and width may be at the lower end of the range, e.g., down to 0.30 mil and 1.0 mil, respectively. Currently available ribbons include sizes of 0.75 mil×4 mil, 1 mil×3 mil, 1 mil×4 mil, 2 mil×6 mil, and 2 mil×8 m The ribbons making up the braid (266) shown in FIG. 7 may also contain a minor amount of non-super-elastic alloy materials. Although metallic ribbons are preferred as the ancillary materials because of their strength-to-weight ratios, fibrous materials (both synthetic and natural) may also be used. Suitable nonmetallic ribbons include high performance materials such as those made of polyaramids (e.g., KEVLAR), liquid crystal polymers (LCP's), and carbon fibers. Preferred, because of cost, strength, and ready availability are stainless steels (SS304, SS306, SS308, SS316, SS318, etc.) and tungsten alloys. In certain applications, particularly smaller diameter catheter sections, more malleable metals and alloys, e.g., gold, platinum, palladium, rhodium, etc. may be used. A platinum alloy with a few percent of tungsten is preferred partially because of its radio-opacity.

The braids utilized in this invention may be made using commercially available tubular braiders. The term "braid" is meant to include tubular constructions in which the ribbons making up the construction are woven radially in an in-and-out fashion as they cross to form a tubular member defining a single lumen. The braids may be made up of a suitable number of ribbons, typically six or more. Ease of production on a commercial braider typically results in braids having eight or sixteen ribbons.

The braid shown in FIG. 5 has a nominal pitch angle (to the catheter axis) of 45°. Clearly the invention is not so limited. Other braid angles from 7.5° to 60° are also suitable. Preferred angles in the distal section are 8.5° to 15°. An important variation of this invention is the ability to vary the pitch angle of the braid either at the time the braid is woven or at the time the braid is included in the catheter section or sections.

The variations depicted herein have each shown a single-ribbon wind. Single-ribbon winds permit the braid to contain the maximum amount of open area between ribbons in the braid. However, the catheter section need not be made with a single wind. The inventive catheter section may have a double-ribbon or other wind. In a double-wind variation, a pair of ribbons is placed side by side and treated as the single ribbon was in the variation shown in FIGS. 7. This variation produces a braid which is denser than the single-ribbon wind. It is also thicker. Typically, the regions between adjacent winds are smaller. The invention described herein is intended to encompass multiple-wind braids. However, some of the benefits of the invention are diminished as the density of the ribbons in the catheter section is increased. That is to say that the stiffness of the catheter section substantially increases as the number of ribbons used in a multiple-ribbon weave is increased.

Distal braid member (262) as was noted above, may either be an extension of the structure of the more proximal braid member (266) or may be an independent braid. In either event, the number of members or ribbons making the distal braid (262) desirably is about half the number of members or ribbons making up braid (266). That is to say that in typical construction, proximal braid (266) would have eight ribbon members woven into the braid; distal braid (262) would have four members woven into braid. The pitch between members would be therefore desirably, but not necessarily, twice that of the more proximal braid. It is preferable that the ribbons in this braid (262) be of stainless steel ribbon. These ribbons are desirably of stainless steel such as (SS304, SS306, SS308, SS316, SS318, etc.). Preferred is SS304V, which is vacuum melded. A highly desirable range of ribbon sizes for use in treatment of neurovascular conditions are ribbons in the range of 0.50 mils to 2.0 mils with a width of 1 mils to 4.0 mils.

Finally, inner liner (268) is shown defining the inner lumen of the catheter. Inner movement (268) is preferably a lubricious polymer.

Preferred materials for the inner liner (268) include the lubricious polymers such as fluoropolymers such as polytetrafluoroethylene (PTFE or TFE), ethylenechlorofluoroethylene (ECTFE), fluorinated ethylene propylene (FEP), polychlorotrifluoroethylene (PCTFE), polyvinylfluoride (PVF), or polyvinylidenefluoride (PVDF). Especially preferred is TFE. Other polymeric materials suitable for the inner liner (268) include polyethylene, polypropylene, polyvinyl chloride (PVC), ethyl vinyl acetate (EVA), polyurethanes, polyamnides, polyethylene terephthalate (PET), and their mixtures and copolymers.

Typically, the distal outer covering member (260) is of a material which is heat-shrinkable (e.g., low density polyethylene) or may otherwise be coated onto the structure (e.g., polyurethanes) onto the inner member (268) and the braids (262, 266). Preferably, the more distal covering (260) comprises a block copolymer of a polyether and a polyamide (e.g., a Pebax). The preferred Shore Hardness of the polymers in the most distal covering (260) is between 70A and 90A.

Another useful class of polymers it the thermoplastic elastomers, including those containing polyesters as components. Typical of this class is HYTREL. Additionally, an adhesive may be coated onto the outer surface of the inner liner tubing. Polyesters and polyimides, in particular, are suitable as adhesives.

An outer covering of polyethylene or of EVA or their mixtures, copolymers, etc. are excellent choices for the outer covering member. The polymer to be used as the outer covering is typically extruded into a tubing of appropriate size and thickness and then cross-linked to raise the melt temperature of the resulting tubing. The tubing is then inflated and perhaps stretched to give the included polymer a specific molecular orientation. The tubing, so treated, may then be slipped over the combination of inner liner (268) and braids (262, 266) and heat shrunk into place.

The material making up more proximal covering (264) may be of the same material as is the distal covering (260). Desirably, in the variation shown in FIG. 7, the hardness is Shore 55D to 75D.

We have found that when a fluorinated polymer is used as the inner tubing member (268), it may be useful to etch the outside surface of the member to provide a good mechanical surface (with "tooth") to which the adjacent polymers will adhere. Certain procedures using, for instance, aliphatic hydrocarbons and sodium metal as the etching solution are known to be effective in such service.

Figure 8:
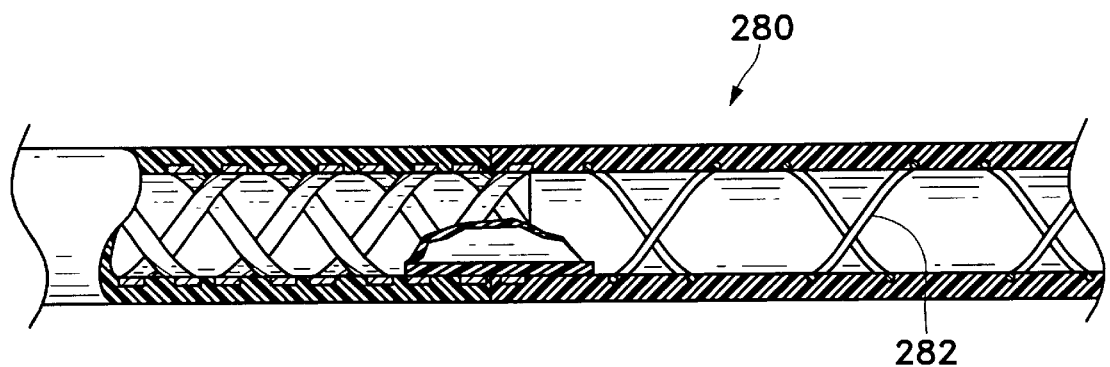

FIG. 8 shows another variation (280) of the distal tip of the inventive device similar to that shown in FIG. 7. The most significant difference between the variation shown in FIG. 8 and that of FIG. 7 is found in the fact that the distal woven braid (282) is comprised of a wire rather than the ribbon braid (262) shown in FIG. 7. Woven wire braid (282) may be of a superelastic alloy such as those described above, but preferably is of a stainless steel material. Highly preferred are braids comprised of wires of stainless steel having a diameter between 0.5 mils to 3 mils. The preferred stainless steel of those listed above is 304V.

While discussing polymeric materials suitable for use in the inventive catheter assembly, it should be noted that the polymeric coverings found in the more proximal coverings of the variations shown in FIG. 2 (210), FIG. 3 (238) and FIG. 4 (258), are preferably materials which are compatible with those placed more distally during the construction. Again, the preferred material is a Pebax, and the Shore Hardness is 35D to 75D. A variety of other polymers may be used. For instance, the noted proximal outer tubing may be a polyamide, polyamides (such as the Nylons), high density polyethylene (HDPE), polypropylene, polyvinylchloride, various fluorocarbon polymers (for instance: PTFE, FEP, vinylidene fluoride, their mixtures, alloys, copolymers, block copolymers, etc.), polysulfones, or the like. Blends, alloys, mixtures, copolymers and block copolymers of these materials are also suitable if desired.

If a more flexible section is required, the noted outer proximal tubing member may also be of a member selected from a more flexible material such as polyurethanes, low density polyethylene (LDPE), polyvinylchloride, THV, etc. and other polymers of suitable softness or a modulus of elasticity.

We have found that when using polyurethane as either the outer covering member, a suitable method for applying the polyurethane to the braid entails placement of a polyurethane tubing over the braid, placement of a polyethylene "shrink-wrappable" tubing over the polyurethane tubing, and heating the combination to pull the polyurethane down to the braid surface using the polyethylene tubing as the mover. The polyethylene may be removed or left in place.

The wall thickness of each of the outer tubing members discussed here may be as thin as 0.5 mils. and as thick as 10 mils., depending upon catheter usage, section of the catheter chosen, polymer choice, and style of catheter.

Typically, a wall thickness of the inner liner (264) will be between 0.5 and 3.0 mils. These dimensions are obviously only ranges and each catheter variation must be carefully designed for the specific purpose to which it is placed.

Each of the polymers noted herein may be used in conjunction with radio-opaque filler materials such as barium sulfate, bismuth trioxide, bismuth carbonate, powdered tungsten, powdered tantalum, or the like so that the location of various portions of the catheter sections may be radiographically visualized within the human body.

It is also within the scope of this invention to coat at least a portion of the exterior surface of the catheter assembly with a lubricious and typically hydrophilic layer, which either is chemically bonded to the adjacent layer or is physically coated on the relevant surface. A description of suitable procedures for producing such lubricious coatings is found at U.S. patent application Ser. Nos. 08/060,401 ("LUBRICIOUS CATHETERS"), filed May 12, 1993 08/235,840 (METHOD FOR PRODUCING LUBRICIOUS CATHETERS"), filed Apr. 29, 1995; and 08/272,209 ("LUBRICIOUS FLOW DIRECTED CATHETER"), filed Jul. 8, 1994, the entirety of which are incorporated by reference.

Figure 9:
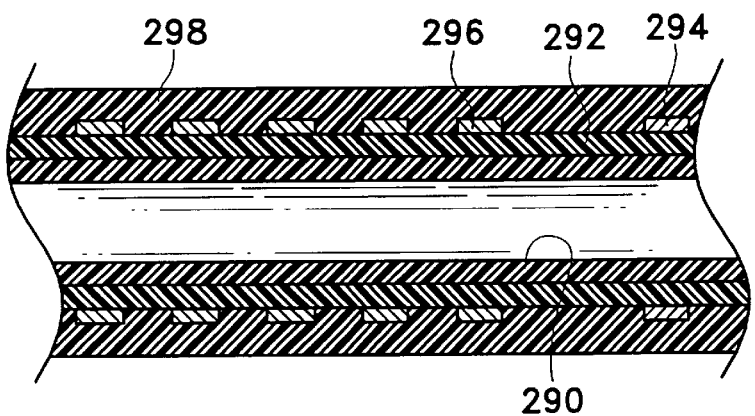
FIG. 9 shows, in magnified cross-section, an inner portion of a catheter section using this invention.

FIG. 9 shows a typical and preferred way of utilizing an inner liner (290) of a lubricious material in conjunction with polyurethane (e.g. Pebax or the like). We have found that lubricious polymeric liner (290) is much more stable in place when attached to polyurethane using an auxiliary layer (292) between that inner liner (290) and distal braid member (294) and proximal braid member (296). The outer liner of polyurethane (298) forms a more consistent, smooth, and constant layer when assembled in this manner.

This invention has been described and specific examples of the invention have portrayed. The use of those specifics is not intended to limit the invention in any way. Additionally, to the extent that there are variations of the invention which are within the spirit of the disclosure and yet are equivalent to the inventions found in the claims, it is our intent that those claims cover those variations as well.

We claim as our invention:

1. A catheter assembly comprising an elongate tubular member having a proximal end, a distal end, an axis, and a passageway defining an inner lumen extending between those ends, comprising
   a.) a relatively less flexible and more proximal segment, comprising
      i.) a more proximal braid member having a proximal end and a distal end, woven of a plurality of proximal braid ribbons, at least a majority of which ribbons comprise a super-elastic alloy, and having inner and outer surfaces,
      ii.) at least one inner lining member comprising a lubricious polymer located interior to said more proximal braid member, and
      iii.) at least one outer covering member comprising a polymer located exterior to said more proximal braid member, and
   b.) a relatively more flexible and more distal tubular segment comprising:
      i.) a more distal braid member, having a proximal end and a distal end, woven of a plurality of more distal braid elements, said more distal braid elements being comparatively fewer in number than said more proximal braid ribbons, and having inner and outer surfaces,
      ii.) at least one inner lining member comprising a lubricious polymer located interior to said more distal braid member, and
      iii.) at least one outer covering member exterior comprising a polymer located exterior to said more distal braid member.

2. The catheter assembly of claim 1 wherein said more distal braid member is discrete.

3. The catheter assembly of claim 2 wherein the proximal end of said more distal braid member is contiguous with the distal end of said more proximal braid member.

4. The catheter assembly of claim 2 wherein said more distal braid elements are stainless steel ribbons.

5. The catheter assembly of claim 2 wherein said more distal braid elements are stainless steel wires.

6. The catheter assembly of claim 2 wherein said more distal braid elements are super-elastic alloy ribbons.

7. The catheter assembly of claim 2 wherein said more distal braid elements are super-elastic alloy wires.

8. The catheter assembly of claim 1 wherein said more distal braid member is a continuation of said more proximal braid member wherein said more distal braid elements being continuations of said proximal braid ribbons.

9. The catheter assembly of claim 1 wherein said inner lining members of said more proximal segment and of said more distal segment are a single tubing element.

10. The catheter assembly of claim 1 wherein said at least one outer covering member exterior to said more proximal braid member comprises at least two polymeric tubing members located along the axis of said catheter assembly with respect to each other.

11. The catheter assembly of claim 1 wherein said at least one outer covering member exterior to said more distal braid member comprises at least two polymeric tubing members located along the axis of said catheter assembly with respect to each other.

12. The catheter assembly of claim 1 wherein said more distal braid member has four braid elements and said more proximal braid member has eight braid ribbons.

13. The catheter assembly of claim 1 where the more proximal braid ribbons have a thickness between 0.5 mil and 3.5 mil and a width between 2.5 and 12.0 mil.

14. The catheter assembly of claim 1 wherein at least one of the at least one outer covering members exterior to said more proximal braid member and said more distal braid member contains a radio-opacifier.

15. The catheter assembly of claim 1 wherein at least one polymeric inner lining member interior comprises polytetrafluoroethylene.

16. The catheter assembly of claim 1 where the more distal braid member braid elements have a spacing and said spacing becomes wider distally.

17. A catheter assembly comprising an elongate tubular member having a proximal end, a distal end, an axis, and a passageway defining an inner lumen extending between those ends, comprising
   a.) a relatively less flexible and more proximal segment, comprising
      i.) a more proximal braid member having a proximal end and a distal end, woven of a plurality of proximal braid ribbons, at least a majority of which ribbons comprise a super-elastic alloy, and having inner and outer surfaces,
      ii.) at least one inner lining member comprising a lubricious polymer located interior to said more proximal braid member, and
      iii.) at least one outer covering member comprising a polymer located exterior to said more proximal braid member, and
   b.) a relatively more flexible and more distal tubular segment comprising:
      i.) a more distal braid member, having a proximal end and a distal end, woven of a plurality of more distal braid elements, said more distal braid elements having a spacing which increases distally, and having inner and outer surfaces,
      ii.) at least one inner lining member comprising a lubricious polymer located interior to said more distal braid member, and
      iii.) at least one outer covering member exterior comprising a polymer located exterior to said more distal braid member.

18. The catheter assembly of claim 17 wherein said more distal braid member is discrete.

19. The catheter assembly of claim 18 wherein the proximal end of said more distal braid member is contiguous with the distal end of said more proximal braid member.

20. The catheter assembly of claim 18 wherein said more distal braid elements are stainless steel ribbons.

21. The catheter assembly of claim 18 wherein said more distal braid elements are stainless steel wires.

22. The catheter assembly of claim 18 wherein said more distal braid elements are super-elastic alloy ribbons.

23. The catheter assembly of claim 18 wherein said more distal braid elements are super-elastic alloy wires.

24. The catheter assembly of claim 17 wherein said more distal braid member is a continuation of said more proximal braid member wherein said more distal braid elements being continuations of said proximal braid ribbons.

25. The catheter assembly of claim 17 wherein said inner lining members of said more proximal segment and of said more distal segment are a single tubing element.

26. The catheter assembly of claim 17 wherein said at least one outer covering member exterior to said more proximal braid member comprises at least two polymeric tubing members located along the axis of said catheter assembly with respect to each other.

27. The catheter assembly of claim 17 wherein said at least one outer covering member exterior to said more distal braid member comprises at least two polymeric tubing members located along the axis of said catheter assembly with respect to each other.

28. The catheter assembly of claim 17 wherein said more distal braid member has four braid elements and said more proximal braid member has eight braid ribbons.

29. The catheter assembly of claim 17 where the more proximal braid ribbons have a thickness between 0.5 mil and 3.5 mil and a width between 2.5 and 12.0 mil.

30. The catheter assembly of claim 17 wherein at least one of the at least one outer covering members exterior to said more proximal braid member and said more distal braid member contains a radio-opacifier.

31. The catheter assembly of claim 17 wherein at least one polymeric inner lining member interior comprises polytetrafluoroethylene.

* * * * *